United States Patent
Yee (10) Patent No.: US 10,045,449 B1
(45) Date of Patent: Aug. 7, 2018

(54) ADJUSTABLE FACIAL-INTERFACE SYSTEMS FOR HEAD-MOUNTED DISPLAYS

(71) Applicant: Oculus VR, LLC, Menlo Park, CA (US)

(72) Inventor: Phillip Yee, San Francisco, CA (US)

(73) Assignee: Oculus VR, LLC, Menlo Park, CA (US)

( * ) Notice: Subject to any disclaimer, the term of this patent is extended or adjusted under 35 U.S.C. 154(b) by 0 days.

(21) Appl. No.: 15/638,334

(22) Filed: Jun. 29, 2017

(51) Int. Cl.
| | |
|---|---|
| *H05K 5/02* | (2006.01) |
| *H05K 5/00* | (2006.01) |
| *A61F 9/02* | (2006.01) |
| *G02B 27/01* | (2006.01) |

(52) U.S. Cl.
CPC ............. *H05K 5/0217* (2013.01); *A61F 9/02* (2013.01); *A61F 9/025* (2013.01); *A61F 9/026* (2013.01); *G02B 27/017* (2013.01); *G02B 27/0176* (2013.01); *H05K 5/0017* (2013.01); *H05K 5/0086* (2013.01)

(58) Field of Classification Search
CPC ... G02B 27/017; G02B 27/0176; A61F 9/025; A61F 9/026; A61F 9/02
See application file for complete search history.

(56) References Cited

U.S. PATENT DOCUMENTS

| | | | |
|---|---|---|---|
| 3,406,589 A | 10/1968 | Gaber | |
| 3,492,037 A | 1/1970 | Hutchinson | |
| 3,704,353 A | 11/1972 | Halla | |
| 5,004,276 A | 4/1991 | Hanley | |
| 5,657,969 A | 8/1997 | Bivens | |
| 5,724,119 A * | 3/1998 | Leight | ..................... A61F 9/025 351/119 |
| 5,739,797 A * | 4/1998 | Karasawa | ............ G02B 27/017 345/8 |
| 5,739,893 A * | 4/1998 | Karasawa | .......... G02B 27/0176 351/158 |

(Continued)

OTHER PUBLICATIONS

Phillip Yee et al.; Adjustable Facial-Interface Systems for Head-Mounted Displays; U.S. Appl. No. 15/637,366, filed Jun. 29, 2017.

(Continued)

*Primary Examiner* — Binh Tran
*Assistant Examiner* — Douglas Burtner
(74) *Attorney, Agent, or Firm* — FisherBroyles, LLP (57) ABSTRACT

A facial-interface system for a head-mounted display may include (1) a facial interface having a positioning abutment surface and (2) a facial-interface adjustment apparatus. The facial-interface adjustment apparatus may include a positioning member that is rotatable about a pivot, the positioning member comprising an extending surface and a contracting surface. The facial-interface adjustment apparatus may also include an actuation member that that is movable to rotate the positioning member about the pivot between (1) an extended holding position in which the extending surface of the positioning member faces and abuts the positioning abutment surface of the facial interface, and (2) a contracted holding position in which the contracting surface of the positioning member faces and abuts the positioning abutment surface of the facial interface. Various other systems, devices, and methods are also disclosed.

20 Claims, 6 Drawing Sheets

(56) References Cited

U.S. PATENT DOCUMENTS

| | | | |
|---|---|---|---|
| 5,752,276 A * | 5/1998 | Baudou | A42B 3/042 2/422 |
| 5,752,280 A * | 5/1998 | Hill | A42B 3/185 2/453 |
| 6,421,031 B1 * | 7/2002 | Ronzani | G02B 27/017 345/8 |
| 6,424,321 B1 * | 7/2002 | Ronzani | G02B 27/017 345/102 |
| 6,669,250 B1 | 12/2003 | St. Louis | |
| 6,762,885 B1 * | 7/2004 | Ogasawara | G02B 27/0176 345/8 |
| 6,892,393 B1 * | 5/2005 | Provost | A42B 3/185 2/10 |
| 7,667,962 B2 | 2/2010 | Mullen | |
| 7,904,128 B2 | 3/2011 | Harmon et al. | |
| 8,971,023 B2 | 3/2015 | Olsson | |
| 9,423,842 B2 | 8/2016 | Osterhout | |
| 9,442,522 B2 | 9/2016 | Tussy | |
| 9,585,285 B2 | 2/2017 | Nikkhoo | |
| 9,757,534 B2 * | 9/2017 | Lang | A61M 16/0633 |
| 9,889,266 B2 * | 2/2018 | Lang | A61M 16/0633 |
| 2002/0005819 A1 * | 1/2002 | Ronzani | G02B 27/017 345/8 |
| 2002/0129433 A1 * | 9/2002 | Shin | A42B 1/247 2/10 |
| 2007/0075918 A1 * | 4/2007 | Cuprys | F41G 3/165 345/8 |
| 2008/0158506 A1 * | 7/2008 | Fuziak | G02B 27/0172 351/158 |
| 2009/0066607 A1 * | 3/2009 | Yasuda | G02B 27/0176 345/8 |
| 2009/0135506 A1 * | 5/2009 | Willey | A42B 3/042 359/815 |
| 2011/0194065 A1 * | 8/2011 | Belbey | A61F 9/025 351/60 |
| 2011/0225709 A1 * | 9/2011 | Saylor | A61F 9/025 2/431 |
| 2013/0249776 A1 * | 9/2013 | Olsson | G06F 1/163 345/8 |
| 2014/0157496 A1 * | 6/2014 | Ginther | A61F 9/025 2/439 |
| 2015/0103306 A1 * | 4/2015 | Kaji | G02C 5/045 351/128 |
| 2015/0219901 A1 * | 8/2015 | Morimoto | G02B 27/017 345/8 |
| 2015/0346494 A1 * | 12/2015 | Tanaka | G02B 27/017 345/647 |
| 2016/0041394 A1 * | 2/2016 | Tanaka | G02B 27/0172 359/630 |
| 2016/0050345 A1 * | 2/2016 | Longbotham | G02B 27/017 348/47 |
| 2016/0124230 A1 * | 5/2016 | Hino | G02B 27/0172 359/214.1 |
| 2016/0147069 A1 * | 5/2016 | Tanaka | G02B 27/0172 359/632 |
| 2016/0193070 A1 * | 7/2016 | Castillo | A61F 5/08 606/204.45 |
| 2017/0326322 A1 * | 11/2017 | Lang | A61M 16/0875 |

OTHER PUBLICATIONS

Sullivan et al.; Facial-Interface Systems for Head-Mounted Displays; U.S. Appl. No. 15/495,775, filed Apr. 24, 2017.

Phillip Yee et al.; Adjustable Facial-Interface Systems for Head-Mounted Displays; U.S. Appl. No. 15/652,550, filed Jul. 18, 2017.

Phillip Yee et al.; Adjustable Facial-Interface Systems for Head-Mounted Displays; U.S. Appl. No. 15/652,565, filed Jul. 18, 2017.

* cited by examiner

ADJUSTABLE FACIAL-INTERFACE SYSTEMS FOR HEAD-MOUNTED DISPLAYS

BACKGROUND

Putting on a virtual reality headset may be the beginning of a thrilling experience, one that may be more immersive than almost any other digital entertainment or simulation experience available today. Virtual reality headsets may enable users to travel through space and time, interact with friends in a three-dimensional world, or play video games in a radically redefined way. Virtual reality headsets may also be used for purposes other than recreation-governments may use them for military training simulations, doctors may use them to practice surgery, and engineers may use them as visualization aids.

Conventional virtual reality headsets often include cushioned facial interfaces that allow users to position the headsets on their faces. However, a particular cushioned facial interface may not comfortably fit users having various head or face shapes or users who also wear glasses while wearing head-mounted displays. Unfortunately, in order to adjust the fit of a facial interface, users must typically remove a facial-interface cushion from a facial interface and replace it with a cushion of a different size to obtain a desired fit. Accordingly, users often cannot properly adjust the fit of a headset without having a replacement facial interface or interface cushion available.

SUMMARY

As will be described in greater detail below, the instant disclosure generally relates to adjustable facial-interface systems for head-mounted displays, head-mounted-display devices, and methods for assembling adjustable facial-interface systems. In one example, a facial-interface system for a head-mounted display may include (1) a facial interface having a positioning abutment surface and (2) a facial-interface adjustment apparatus. The facial-interface adjustment apparatus may include a positioning member that is rotatable about a pivot, and the positioning member may include an extending surface and a contracting surface. The facial-interface adjustment apparatus may also include an actuation member that that is movable to rotate the positioning member about the pivot between (1) an extended holding position in which the extending surface of the positioning member faces and abuts the positioning abutment surface of the facial interface, and (2) a contracted holding position in which the contracting surface of the positioning member faces and abuts the positioning abutment surface of the facial interface. Various other systems, devices, and methods are also disclosed.

In some embodiments, the contracting surface may extend from a region adjacent the extending surface to a portion of the positioning member adjacent the pivot. The facial interface may be movable between the extended holding position and the contracted holding position in a direction generally perpendicular to an axis of rotation of the positioning member about the pivot. In at least one example, the positioning member may be a wedge-shaped member tapering from the extending surface to a pivot region surrounding the pivot and the extending surface may have a greater width than the pivot region. The actuation member may be movable in a direction generally perpendicular to the axis of rotation of the positioning member about the pivot. In some examples, the actuation member may include a shaft portion that extends in a direction generally perpendicular to an axis of rotation of the positioning member about the pivot.

According to at least one embodiment, the facial-interface adjustment apparatus may further include a spring that is coupled to the actuation member. In this example, the spring may be disposed between the actuation member and the facial interface. Additionally or alternatively, the spring may be relaxed when the positioning member is disposed in the extended holding position and the spring may be tensioned when the positioning member is disposed in the contracted holding position. In some examples, the facial-interface system may further include a restraining protrusion extending from the positioning abutment surface and the contracting surface of the positioning member may face the restraining protrusion when the positioning member is disposed in the extended holding position.

According to some embodiments, the positioning member may be a primary positioning member, the pivot may be a primary pivot, and the facial-interface adjustment apparatus may further include a secondary positioning member that is rotatable about a secondary pivot (the secondary positioning member may have an extending surface and a contracting surface). In this example, the actuation member may be movable to simultaneously rotate the secondary positioning member about the secondary pivot in conjunction with the rotation of the primary positioning member about the primary pivot such that the secondary positioning member rotates between (1) an extended holding position in which the extending surface of the secondary positioning member faces and abuts the positioning abutment surface of the facial interface, and (2) a contracted holding position in which the contracting surface of the secondary positioning member faces and abuts the positioning abutment surface of the facial interface.

In at least one embodiment, the facial-interface system may further include a positioning-member connector that is connected to the primary positioning member and the secondary positioning member. In this example, the positioning-member connector may be connected to the extending surface of the primary positioning member and the extending surface of the secondary positioning member. Additionally or alternatively, the positioning-member connector may include a flexible material that folds as each of the primary positioning member and the secondary positioning member rotates from the extended holding position to the contracted holding position. The actuation member may be coupled to the positioning-member connector at a location between the primary positioning member and the secondary positioning member. In some examples, the actuation member may simultaneously rotate the primary positioning member and the secondary positioning member in opposite rotational directions.

A corresponding head-mounted-display device may include (1) a head-mounted-display housing, (2) a facial interface having a positioning abutment surface, (3) and a facial-interface adjustment apparatus that is coupled to the head-mounted-display housing. In this example, the facial interface may be disposed at a separate location relative to the head-mounted-display housing when the positioning member is disposed in each of the extended holding position and the contracted holding position.

A corresponding method may include positioning a positioning abutment surface of a facial interface adjacent to a facial-interface adjustment apparatus, and the facial-interface adjustment apparatus may include (1) a positioning member that is rotatable about a pivot (the positioning member may include an extending surface and a contracting surface) and (2) an actuation member that is movable to rotate the positioning member about the pivot between (i) an extended holding position in which the extending surface of the positioning member faces and abuts the positioning abutment surface of the facial interface such that the positioning abutment surface is disposed at an extended radial distance from the pivot, and (ii) a contracted holding position in which the contracting surface of the positioning member faces and abuts the positioning abutment surface of the facial interface such that the positioning abutment surface is disposed at a contracted radial distance from the pivot that is less than the extended radial distance.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure describes various adjustable facial-interface systems for head-mounted displays, head-mounted-display devices, and methods for assembling adjustable facial-interface systems. As will be explained in greater detail below, embodiments of the instant disclosure may include facial-interface systems having facial-interface adjustment apparatuses that enable users to quickly and easily adjust facial interfaces. The facial-interface adjustment apparatuses may include one or more positioning members that are rotatable between an extended holding position that holds a facial interface at an extended holding position and a contracted holding position that holds a facial interface at a contracted holding position. The facial-interface systems may thus enable users to position the facial interfaces so as to comfortably fit head-mounted displays to various user face sizes and shapes. The facial-interface systems may also enable users to wear accessories, such as glasses, while wearing the head-mounted displays. Accordingly, the facial-interface systems may allow users to adjust and comfortably wear head-mounted displays without having to replace the facial interfaces and/or interface cushions.

Figure 1:
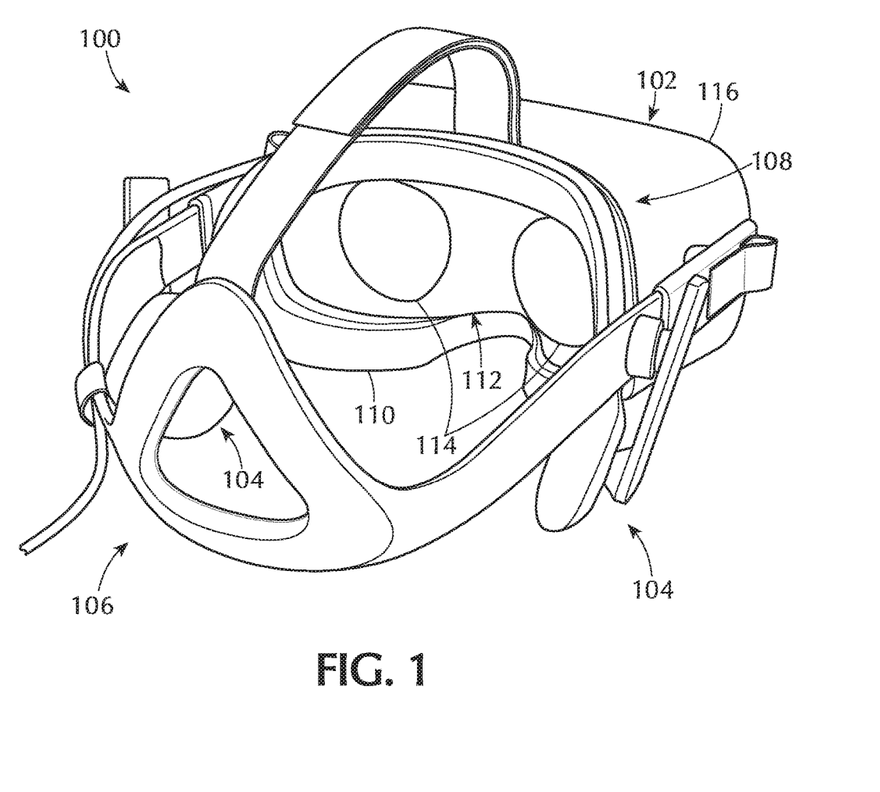
FIG. 1 is a perspective view of an exemplary head-mounted-display system in accordance with some embodiments.
Figure 2:
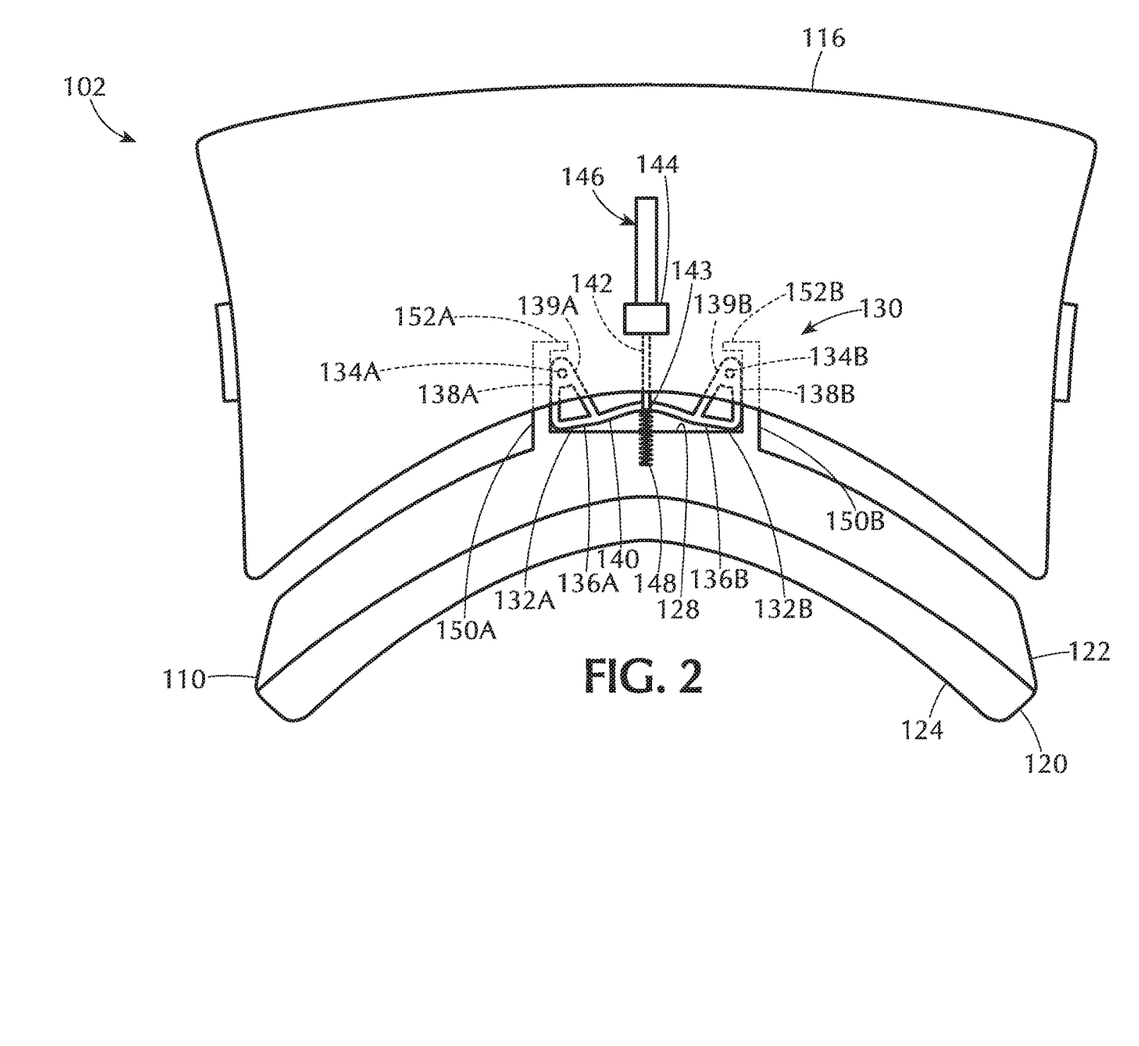
FIG. 2 is a top view of an exemplary head-mounted-display device in accordance with some embodiments.
Figure 3:
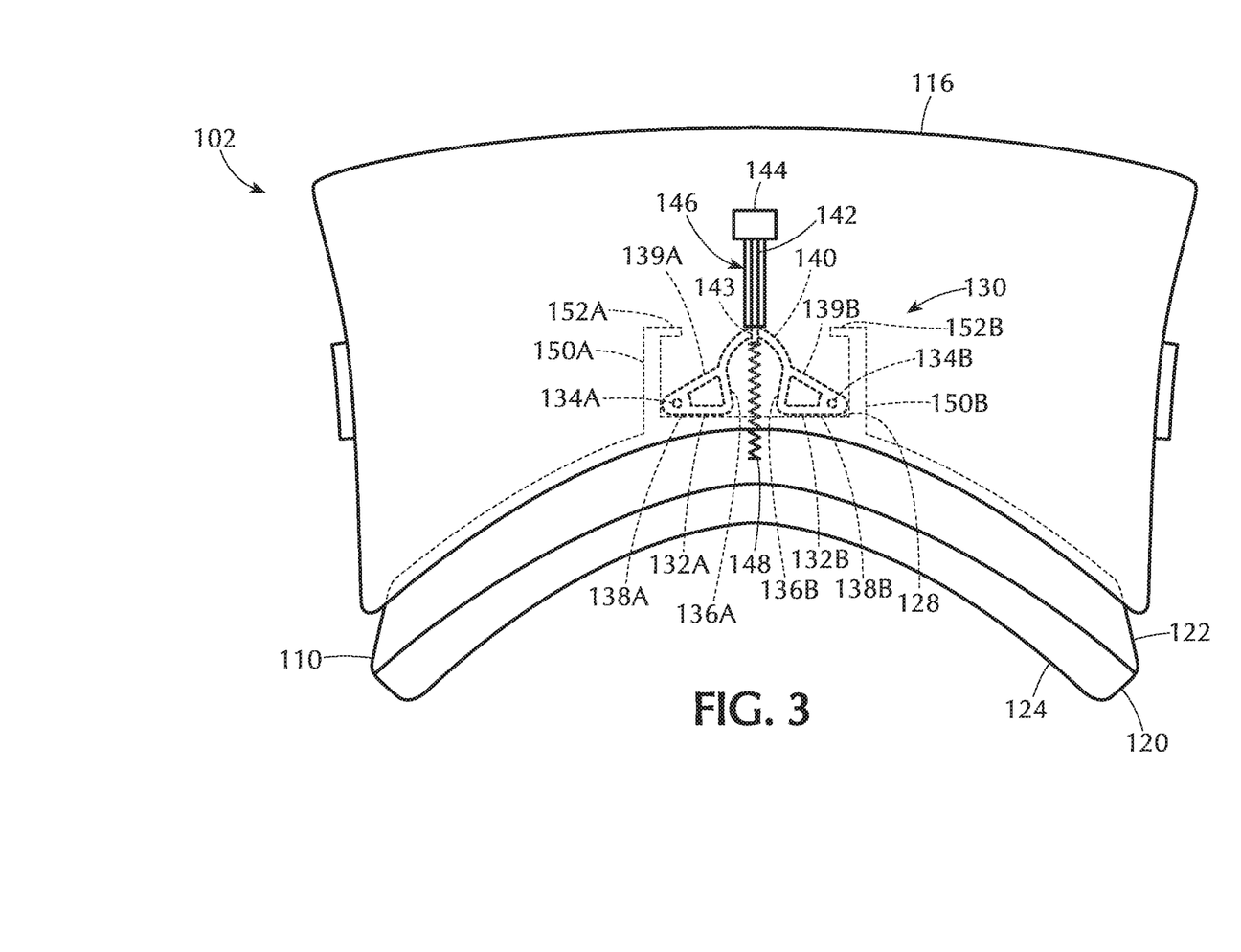
FIG. 3 is a top view of an exemplary head-mounted-display device in accordance with some embodiments.

The following will provide, with reference to FIGS. 1-3, examples of head-mounted-display systems and head-mounted-display devices that include adjustable facial-interface systems. In addition, the discussion corresponding to FIGS. 4-5 will provide examples of adjustable facial-interface systems. The discussion corresponding to FIGS. 6-7 will also provide examples of head-mounted-display devices that include adjustable facial-interface systems. Finally, the discussion corresponding to FIG. 8 will provide examples of methods for assembling adjustable facial-interface systems.

FIG. 1 is a perspective view of a head-mounted-display system 100 in accordance with some embodiments. In some embodiments, head-mounted-display system 100 may include a head-mounted-display device 102 (i.e., head-mounted display), audio subsystems 104, a strap assembly 106, and a facial-interface system 108. The term "head-mounted display," as used herein, generally refers to any type or form of display device or system that is worn on or about a user's head and displays visual content to the user. Head-mounted displays may display content in any suitable manner, including via a screen (e.g., an LCD or LED screen), a projector, a cathode ray tube, an optical mixer, etc. Head-mounted displays may display content in one or more of various media formats. For example, a head-mounted display may display video, photos, and/or computer-generated imagery (CGI). Head-mounted-display device 102 may include a head-mounted-display housing 116 surrounding various components of head-mounted-display device 102, including lenses 114 and various electronic components, including display components as described above.

Head-mounted displays may provide diverse and distinctive user experiences. Some head-mounted displays may provide virtual-reality experiences (i.e., they may display computer-generated or pre-recorded content), while other head-mounted displays may provide real-world experiences (i.e., they may display live imagery from the physical world). Head-mounted displays may also provide any mixture of live and virtual content. For example, virtual content may be projected onto the physical world (e.g., via optical or video see-through), which may result in augmented reality or mixed reality experiences. Head-mounted displays may be configured to be mounted to a user's head in a number of ways. Some head-mounted displays may be incorporated into glasses or visors. Other head-mounted displays may be incorporated into helmets, hats, or other headwear. Examples of head-mounted displays may include OCULUS RIFT, GOOGLE GLASS, VIVE, SAMSUNG GEAR, etc.

In some embodiments, audio subsystems 104 may be integrated with head-mounted-display device 102 and may provide audio signals to the user's ears. Head-mounted-display system 100 may, for example, have two audio subsystems 104 located on the left and right sides of head-mounted-display system 100 to provide audio signals to the user's left and right ears, as shown in FIG. 1.

Strap assembly 106 may be used for adjustably mounting head-mounted-display device 102 on the user's head. As shown in FIG. 1, strap assembly 106 may include various straps, such as an upper strap and lower straps, that are coupled to head-mounted-display device 102 to adjustably conform to the top and/or sides of the user's head when the user is wearing head-mounted-display device 102.

In some embodiments, facial-interface system 108 may be configured to comfortably rest against a region of the user's face, including a region surrounding the user's eyes, when head-mounted-display system 100 is worn by the user. In these embodiments, facial-interface system 108 may include a facial interface 110 that contacts selected regions of the user's face. Facial interface 110 may surround a viewing region 112 that includes the user's field of vision while the user is wearing head-mounted-display system 100, allowing the user to look through lenses 114 of head-mounted-display device 102 without interference from outside light while the user is wearing head-mounted-display system 100.

FIGS. 2 and 3 are top views of a head-mounted-display device 102 that includes a facial-interface adjustment apparatus 130. FIG. 2 illustrates facial-interface adjustment apparatus 130 in an extended holding position and FIG. 3 illustrates facial-interface adjustment apparatus 130 in a contracted holding position. FIG. 2 shows facial interface 110 disposed outside of head-mounted-display housing 116 when facial-interface adjustment apparatus 130 is in the extended holding position. Additionally or alternatively, at least a portion of facial interface 110 may be disposed within head-mounted-display housing 116 when facial-interface adjustment apparatus 130 is in the extended holding position and/or the contracted holding position.

As shown in FIGS. 2 and 3, facial interface 110 may include an interface cushion 120 mounted to an interface mounting member 122. In some embodiments, interface cushion 120 may include or be formed from a pliable material. For example, interface cushion 120 may include or be formed from a foam material (e.g., polyurethane foam) and/or any other pliable material suitable for contacting a facial region of a user and/or suitable for conforming to a shape of interface mounting member 122. In some examples, the pliable material may enable interface cushion 120 to conform to a mounting surface of interface mounting member 122. In at least one example, interface cushion 120 may include multiple cushion layers and/or a covering layer over at least a portion of interface cushion 120. Interface mounting member 122 may be formed of a material having greater rigidity than interface cushion 120, such as a hard or semi-hard polymeric and/or metallic material.

Interface cushion 120 may include a facial-abutment surface 124 that is configured to abut facial regions of the user when head-mounted-display system 100 is worn by the user. For example, facial-abutment surface 124 may be configured to abut at least a portion of the user's nose, cheek, temple, and/or forehead facial regions. Interface cushion 120 may be mounted to interface mounting member 122 at a side of interface cushion 120 opposite facial-abutment surface 124. Facial interface 110 may define a viewing opening, which corresponds to, for example, viewing region 112 illustrated in FIG. 1. Head-mounted-display housing 116 may be shaped and sized to surround various components of head-mounted-display device 102 including lenses 114 shown in FIG. 1 and various electronic components, including display components for displaying images to a user through lenses 114. Head-mounted-display housing 116 may be formed of a hard material, such as a polymeric and/or metallic material, that covers and protects interior components of head-mounted-display device 102. Head-mounted-display housing 116 may include a housing opening adjacent to facial interface 110. In some embodiments, such a housing opening may be shaped and sized to surround and/or abut at least a portion of facial interface 110, including at least a portion of interface mounting member 122.

Facial-interface adjustment apparatus 130 may be coupled to head-mounted-display housing 116 and may be disposed adjacent to and/or abutting at least a portion of facial interface 110. For example, facial-interface adjustment apparatus 130 may abut a portion of interface mounting member 122 at a side of interface mounting member 122 opposite interface cushion 120. Facial-interface adjustment apparatus 130 may include at least one positioning member that changes the position of facial interface 110 relative to head-mounted-display housing 116. For example, as shown in FIGS. 2 and 3, facial-interface adjustment apparatus 130 may include a primary positioning member 132A and a secondary positioning member 132B. Each positioning member may be independently rotatable about a separate pivot. For example, primary positioning member 132A may be rotatable about a primary pivot 134A and secondary positioning member 132B may be rotatable about a secondary pivot 134B. According to some examples, primary positioning member 132A may have an axis of rotation about primary pivot 134A that is substantially parallel to an axis of rotation of secondary positioning member 132B about secondary pivot 134B. Each of the positioning members may include an extending surface and a contracting surface. For example, primary positioning member 132A may include an extending surface 136A and a contracting surface 138A and secondary positioning member 132B may include an extending surface 136B and a contracting surface 138B. Each of the positioning members may also include a positioning support surface that extends between a region adjacent to the corresponding pivot and a region adjacent to a portion of the corresponding extending surface. For example, primary positioning member 132A may include a positioning support surface 139A and secondary positioning member 132B may include a positioning support surface 139B.

In some embodiments, primary positioning member 132A and/or secondary positioning member 132B may each be a wedge-shaped member. For example, primary positioning member 132A may have a wedge shape that tapers from extending surface 136A to a pivot region surrounding primary pivot 134A and secondary positioning member 132B may have a wedge shape that tapers from extending surface 136B to a pivot region surrounding secondary pivot 134B. As shown in FIGS. 2 and 3, for example, contracting surface 138A of primary positioning member 132A may extend from a region adjacent extending surface 136A to a portion of primary positioning member 132A adjacent primary pivot 134A and contracting surface 138B of secondary positioning member 132B may extend from a region adjacent extending surface 136B to a portion of secondary positioning member 132B adjacent secondary pivot 134B. Additionally, positioning support surface 139A of primary positioning member 132A may extend from another region adjacent extending surface 136A to a portion of primary positioning member 132A adjacent primary pivot 134A and contracting surface 138B of secondary positioning member 132B may extend from another region adjacent extending surface 136B to a portion of secondary positioning member 132B adjacent secondary pivot 134B. A distance between contracting surface 138A and positioning support surface 139A of primary positioning member 132A may progressively decrease along a direction from extending surface 136A to primary pivot 134A of primary positioning member 132A. Likewise, a distance between contracting surface 138B and positioning support surface 139B of secondary positioning member 132B may progressively decrease along a direction from extending surface 136B to secondary pivot 134B of secondary positioning member 132B. Extending surface 136A and extending surface 136B may each have a greater width than the corresponding pivot regions of primary positioning member 132A and secondary positioning member 132B respectively surrounding primary pivot 134A and secondary pivot 134B. Primary positioning member 132A and/or secondary positioning member 132B may have any other suitable shape, without limitation, such as, for example, an oblong angular and/or arcuate shape.

As shown in FIG. 2, extending surface 136A and extending surface 136B of primary positioning member 132A and secondary positioning member 132B, respectively, may each be positioned facing and/or abutting a positioning abutment surface 128 of interface mounting member 122 when primary positioning member 132A and secondary positioning member 132B of facial-interface adjustment apparatus 130 are in an extended holding position. In the extended holding position, extending surface 136A and extending surface 136B may hold positioning abutment surface 128 of interface mounting member 122 at an extended position relative to head-mounted-display housing 116 such that positioning abutment surface 128 is disposed at an extended radial distance from primary pivot 134A and/or secondary pivot 134B. Alternatively, as shown in FIG. 3, contracting surface 138A and contracting surface 138B of primary positioning member 132A and secondary positioning member 132B, respectively, may each be positioned facing and/or abutting positioning abutment surface 128 of interface mounting member 122 when primary positioning member 132A and secondary positioning member 132B of facial-interface adjustment apparatus 130 are in a contracted holding position. In the contracted holding position, contracting surface 138A and contracting surface 138B may hold positioning abutment surface 128 of interface mounting member 122 at a contracted position relative to head-mounted-display housing 116 such that positioning abutment surface 128 is disposed at a contracted radial distance from primary pivot 134A and/or secondary pivot 134B that is less than the extended radial distance. Primary positioning member 132A may be rotatable about primary pivot 134A and secondary positioning member 132B may be rotatable about secondary pivot 134B between the extended holding position illustrated in FIG. 2 and the contracted holding position illustrated in FIG. 3, as will be discussed in greater detail below in reference to FIGS. 4 and 5.

In at least one embodiment, facial-interface adjustment apparatus 130 may include at least one actuation member that is movable to rotate primary positioning member 132A and/or secondary positioning member 132B between the extended holding position and the contracted holding position. For example, facial-interface adjustment apparatus 130 may include an actuation member 142 that is movable in a direction generally or substantially perpendicular to an axis of rotation of primary positioning member 132A and/or secondary positioning member 132B. Actuation member 142 may, for example, be movable from the position shown in FIG. 2 to the position shown in FIG. 3 in a direction away from facial interface 110 to rotate primary positioning member 132A and secondary positioning member 132B from the extended holding position to the contracted holding position. Additionally, actuation member 142 may be movable from the position shown in FIG. 3 to the position shown in FIG. 2 in a direction toward facial interface 110 to rotate primary positioning member 132A and secondary positioning member 132B from the contracted holding position to the extended holding position. In some examples, actuation member 142 may include a longitudinally extending member, such as a shaft or shaft portion, that extends in a direction generally or substantially perpendicular to the axis of rotation of primary positioning member 132A and/or secondary positioning member 132B. Actuation member 142 may additionally or alternatively include any other suitable shape, without limitation.

Actuation member 142 may be directly or indirectly coupled to at least a portion of primary positioning member 132A and/or secondary positioning member 132B. According to some embodiments, primary positioning member 132A and secondary positioning member 132B may be coupled to each other by a positioning-member connector 140. As shown in FIGS. 2 and 3, for example, positioning-member connector 140 may extend from primary positioning member 132A to secondary positioning member 132B and positioning-member connector 140 may include a coupling portion 143 that is coupled to a portion of positioning-member connector 140 between primary positioning member 132A and secondary positioning member 132B. In at least one example, positioning-member connector 140 may be integrally formed with primary positioning member 132A and/or secondary positioning member 132B. For example, positioning-member connector 140, primary positioning member 132A, and secondary positioning member 132B may be formed as a single molded component. Additionally or alternatively, positioning-member connector 140 may be separate from primary positioning member 132A and/or secondary positioning member 132B.

Positioning-member connector 140, primary positioning member 132A, and/or secondary positioning member 132B may be formed of a flexible material, such as an elastic polymeric material (e.g., rubber, silicone, etc.) and/or metallic material, that flexes and folds as primary positioning member 132A and secondary positioning member 132B are moved from the extended holding position shown in FIG. 2 to the contracted holding position shown in FIG. 3. In some embodiments, positioning-member connector 140 may be formed of a flexible material and primary positioning member 132A and/or secondary positioning member 132B may be formed of a more rigid material, such as a hard plastic and/or metallic material. As will be described in greater detail below in reference to FIGS. 4 and 5, positioning-member connector 140 may facilitate simultaneous rotation of primary positioning member 132A and secondary positioning member 132B in conjunction with movement of actuation member 142. In some embodiments, positioning-member connector 140 may include one or more rigid connecting members. For example, positioning-member connector 140 may include a first rigid connecting member extending between primary positioning member 132A and actuation member 142 and/or spring 148 and a second rigid connecting member extending between secondary positioning member 132B and actuation member 142 and/or spring 148. In such an example, the first rigid connecting member and the second rigid connecting member may be rotatable relative to primary positioning member 132A, secondary positioning member 132B, actuation member 142, and/or spring 148 such that a portion of the first rigid connecting member coupled to primary positioning member 132A may move closer to a portion of the second rigid connecting member coupled to secondary positioning member 132B as primary positioning member 132A and secondary positioning member 132B are moved from the extended holding position shown in FIG. 2 to the contracted holding position shown in FIG. 3.

According to at least one embodiment, facial-interface adjustment apparatus 130 may also include a sliding member 144 and a sliding-path opening 146 that facilitate movement of actuation member 142 by a user. For example, sliding member 144 may be disposed on an exterior portion of head-mounted-display housing 116 and may be connected to actuation member 142 via sliding-path opening 146. A user may slide sliding member 144 along sliding-path opening 146 to move actuation member 142 between the position shown FIG. 2 and the position shown in FIG. 3.

In some embodiments, facial-interface adjustment apparatus 130 may include a spring 148. For example, spring 148 may be disposed between actuation member 142 and facial interface 110 and/or between primary positioning member 132A and secondary positioning member 132B. In at least one example, spring 148 may be coupled to actuation member 142 and/or facial interface 110. Spring 148 may be any suitable type of spring, such as, for example, an extension spring having a coiled body. Spring 148 may be relaxed when primary positioning member 132A and/or secondary positioning member 132B is in the extended holding position shown in FIG. 2, and spring 148 may be stretched and tensioned when primary positioning member 132A and/or secondary positioning member 132B is in the contracted holding position shown in FIG. 3. As will be explained in greater detail below with reference to FIGS. 4 and 5, spring 148 may exert a biasing force on actuation member 142 and/or positioning-member connector 140 in a direction toward facial interface 110 to facilitate rotation of primary positioning member 132A and/or secondary positioning member 132B from the contracted holding position to the extended holding position and/or to hold facial interface 110 adjacent to primary positioning member 132A and/or secondary positioning member 132B in the contracted holding position. In at least one example, facial-interface adjustment apparatus 130 may not include a spring such as spring 148.

In at least one embodiment, at least one restraining protrusion may protrude from a portion of interface mounting member 122 of facial interface 110. For example, a restraining protrusion 150A and a restraining protrusion 150B may extend from a portion of interface mounting member 122 adjacent to positioning abutment surface 128 such that primary positioning member 132A and secondary positioning member 132B are disposed between restraining protrusion 150A and restraining protrusion 150B. Restraining protrusion 150A and restraining protrusion 150B may movably couple facial interface 110 with at least a portion of facial-interface adjustment apparatus 130. For example, restraining protrusion 150A may include a protrusion coupling portion 152A and restraining protrusion 150B may include a protrusion coupling portion 152B, as shown in FIGS. 2 and 3. Protrusion coupling portion 152A and protrusion coupling portion 152B may enable facial interface 110 to be moved between the extended and contracted positions shown in FIGS. 2 and 3 while preventing separation of facial interface 110 from facial-interface adjustment apparatus 130. Additionally or alternatively, restraining protrusion 150A and/or restraining protrusion 150B may align facial interface 110 with respect to facial-interface adjustment apparatus 130. In some examples, contracting surface 138A of primary positioning member 132A may face and/or abut restraining protrusion 150A and contracting surface 138B of secondary positioning member 132B may face and/or abut restraining protrusion 150B when primary positioning member 132A and secondary positioning member 132B are disposed in the extended holding position, as shown in FIG. 2.

Figure 4:
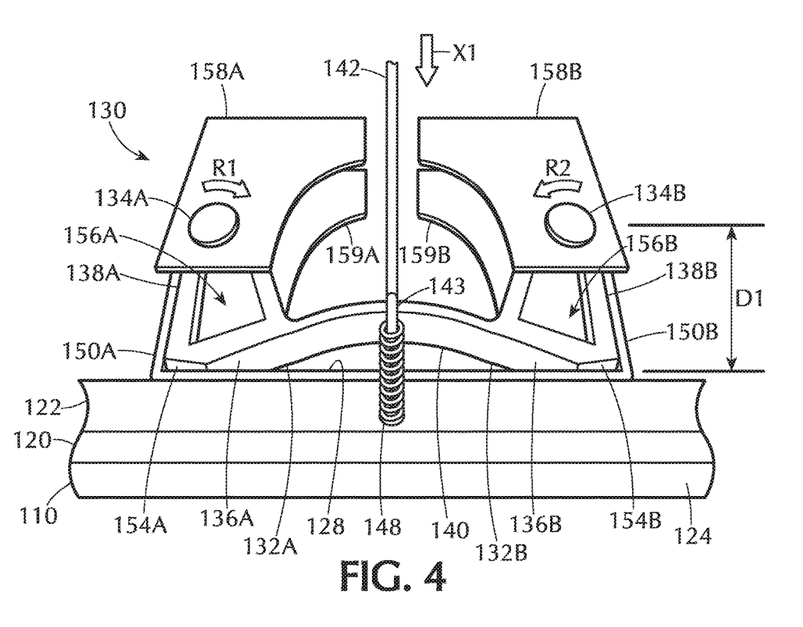
FIG. 4 is a perspective view of a portion of an exemplary facial-interface system in accordance with some embodiments.
Figure 5:
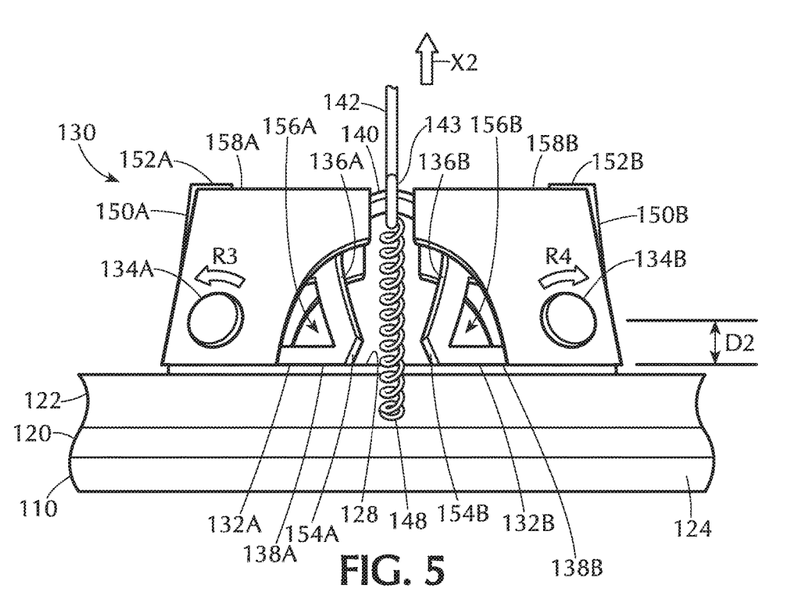
FIG. 5 is a perspective view of a portion of an exemplary facial-interface system in accordance with some embodiments.

FIGS. 4 and 5 are a perspective views of a portion of facial interface 110 and facial-interface adjustment apparatus 130. FIG. 4 shows facial-interface adjustment apparatus 130 in the extended holding position and corresponds to FIG. 2, and FIG. 5 shows facial-interface adjustment apparatus 130 in the contracted holding position and corresponds to FIG. 3. As illustrated in FIGS. 4 and 5, primary positioning member 132A may include a sloped surface 154A between extending surface 136A and contracting surface 138A and secondary positioning member 132B include a sloped surface 154B between extending surface 136B and contracting surface 138B. Sloped surface 154A and sloped surface 154B may facilitate positioning of primary positioning member 132A and secondary positioning member 132B and/or may facilitate rotation of primary positioning member 132A and secondary positioning member 132B between the extended holding position and the contracted holding position. Sloped surface 154A and/or sloped surface 154B may be a sloped (e.g., chamfered) and/or arcuate surface the minimizes the protruding profile of primary positioning member 132A and/or secondary positioning member 132B at an intersection region between extending surface 136A and contracting surface 138A and/or between extending surface 136B and contracting surface 138B. In some embodiments, a positioning-member opening 156A may be defined in primary positioning member 132A and/or a positioning-member opening 156B may be defined in secondary positioning member 132B, reducing the weight of primary positioning member 132A and secondary positioning member 132B and/or minimizing an amount of material required to form primary positioning member 132A and secondary positioning member 132B. In at least one example, positioning-member opening 156A and/or positioning-member opening 156B may enable primary positioning member 132A and/or secondary positioning member 132B to be slightly deformed, thereby facilitating rotational movement and/or positioning of primary positioning member 132A and/or secondary positioning member 132B.

In some embodiments, facial-interface adjustment apparatus 130 may include a casing or support member surrounding and/or supporting at least a portion of facial-interface adjustment apparatus 130. For example, facial-interface adjustment apparatus 130 may include an upper support member 158A and a lower support member 159A respectively positioned on upper and lower portions of primary positioning member 132A such that at least a portion of primary positioning member 132A is disposed between upper support member 158A and lower support member 159A. Additionally, facial-interface adjustment apparatus 130 may include an upper support member 158B and a lower support member 159B respectively positioned on upper and lower portions of secondary positioning member 132B such that at least a portion of secondary positioning member 132B is disposed between upper support member 158B and a lower support member 159B.

Upper support member 158A and a lower support member 159A may hold primary pivot 134A (e.g., primary pivot 134A may extend from upper support member 158A through primary positioning member 132A to lower support member 159A) such that primary positioning member 132A is rotatable about primary pivot 134A between upper support member 158A and lower support member 159A. Additionally or alternatively upper support member 158B and lower support member 159B may hold secondary pivot 134B (e.g., secondary pivot 134B may extend from upper support member 158B through secondary positioning member 132B to lower support member 159B) such that secondary positioning member 132B is rotatable about secondary pivot 134B between upper support member 158B and lower support member 159B. In some embodiments, primary pivot 134A and/or secondary pivot 134B may include a rotatable shaft and/or other suitable pivot member extending through at least a portion of primary positioning member 132A and/or secondary positioning member 132B. In some embodiments, at least a portion of restraining protrusion 150A may be disposed between upper support member 158A and lower support member 159A and/or at least a portion of restraining protrusion 150B may be disposed between upper support member 158B and lower support member 159B such that restraining protrusion 150A and/or restraining protrusion 150B may slide in directions X1 and X2 shown in FIGS. 4 and 5 as facial interface 110 moves in directions X1 and X2.

According to at least one embodiment, facial-interface adjustment apparatus 130 may be adjusted from the contracted holding position illustrated in FIG. 5 to the extended holding position illustrated in FIG. 4. For example, a user may move actuation member 142 in direction X1 shown in FIG. 4 (e.g., by forcing sliding member 144 shown in FIGS. 2 and 3 in direction X1) so as to force positioning-member connector 140 in direction X1. Direction X1 may be perpendicular, or generally perpendicular, to an axis of rotation of primary positioning member 132A and/or secondary positioning member 132B respectively about primary pivot 134A and/or secondary pivot 134B. As positioning-member connector 140 is forced in direction X1, primary positioning member 132A and secondary positioning member 132B may simultaneously rotate about primary pivot 134A and secondary pivot 134B in rotational direction R1 and rotational direction R2, respectively. As shown in FIG. 4, rotational direction R1 may be opposite rotational direction R2. Positioning-member connector 140 may be connected to and/or integrally formed with end portions of extending surface 136A and extending surface 136B to facilitate rotational movement of primary positioning member 132A and secondary positioning member 132B and to facilitate concurrent movement of facial interface 110 in direction X1 as primary positioning member 132A and secondary positioning member 132B are forced against facial interface 110. In some embodiments, spring 148 may further facilitate movement of positioning-member connector 140 in direction X1 by applying tension to actuation member 142 and/or positioning-member connector 140 in direction X1. The tension applied by spring 148 to actuation member 142 and/or positioning-member connector 140 may not be sufficient by itself to force the rotation of primary positioning member 132A and secondary positioning member 132B from the contracted holding position to the extended holding position. Accordingly, facial-interface adjustment apparatus 130 may be held in the contracted holding position shown in FIG. 5 while spring 148 is stretched and tensioned.

In at least one example, the user may adjust facial-interface adjustment apparatus 130 from the contracted holding position shown in FIG. 5 to the extended holding position shown in FIG. 4 by grasping and pulling facial interface 110 in direction X1 instead of or in addition to forcing actuation member 142 in direction X1. For example, the user may pull facial interface 110, which is coupled to an end of spring 148, so as to pull the end of spring 148 coupled to facial interface 110 in direction X1, further stretching and tensioning spring 148. As spring 148 is stretched and tensioned by the user in direction X1, additional force may be applied by spring 148 to actuation member 142 and positioning-member connector 140 in direction X1. Additionally, as the user pulls facial interface 110 in direction X1, positioning abutment surface 128 of interface mounting member 122 may be moved away from primary positioning member 132A and secondary positioning member 132B so that any resistance to rotation of primary positioning member 132A and secondary positioning member 132B by abutting positioning abutment surface 128 may be reduced or eliminated. Accordingly, primary positioning member 132A and secondary positioning member 132B may be rotated in respective rotational directions R1 and R2 as the user pulls facial interface 110 in direction X1, thereby adjusting facial-interface adjustment apparatus 130 from the contracted holding position to the extended holding position.

In the extended holding position illustrated in FIG. 4, extending surface 136A and extending surface 136B of primary positioning member 132A and secondary positioning member 132B may each face and abut positioning abutment surface 128 of facial interface 110 such that positioning abutment surface 128 is disposed at an extended radial distance D1 from primary pivot 134A and/or secondary pivot 134B. When facial-interface adjustment apparatus 130 is in the extended holding position, facial interface 110 may be disposed at an extended position relative to head-mounted-display housing 116 as illustrated, for example, in FIG. 2. Portions of primary positioning member 132A and secondary positioning member 132B forming contracting surface 138A and contracting surface 138B may be disposed between positioning abutment surface 128 and primary pivot 134A and secondary pivot 134B, respectively, so as to securely hold and maintain the position of facial interface 110.

While facial-interface adjustment apparatus 130 is disposed in the extended holding position, a force may be applied by the user's face to facial-abutment surface 124 of facial interface 110 in a direction generally opposite direction X1 (e.g., direction X2 shown in FIG. 5) while the user is wearing a head-mounted-display system (e.g., head-mounted-display system 100 shown in FIG. 1) that includes facial interface 110 and facial-interface adjustment apparatus 130. Direction X2 may be perpendicular, or generally perpendicular, to an axis of rotation of primary positioning member 132A and/or secondary positioning member 132B respectively about primary pivot 134A and/or secondary pivot 134B. Due to the respective orientations of primary positioning member 132A and secondary positioning member 132B when facial-interface adjustment apparatus 130 is in the extended holding position, the force applied by the user's face to facial interface 110 may be transmitted to primary positioning member 132A and secondary positioning member 132B and to primary pivot 134A and secondary pivot 134B without forcing primary positioning member 132A and/or secondary positioning member 132B in a rotational direction, thereby preventing facial-interface adjustment apparatus 130 from moving from the extended holding position shown in FIG. 4 to the contracted holding position shown in FIG. 5. In some embodiments, actuation member 142 may be secured in a fixed position (e.g., by a holding feature in head-mounted-display housing 116 of head-mounted-display device 102) to prevent movement of actuation member 142 and thus maintain facial-interface adjustment apparatus 130 in the extended holding position until the user manually moves actuation member 142 from the fixed position. Accordingly, the user may comfortably and securely mount head-mounted-display system to their head when facial-interface adjustment apparatus 130 is in the extended holding position.

According to some embodiments, facial-interface adjustment apparatus 130 may be adjusted from the extended holding position illustrated in FIG. 4 to the contracted holding position illustrated in FIG. 5. For example, a user may move actuation member 142 in direction X2 shown in FIG. 5 (e.g., by forcing sliding member 144 shown in FIGS. 2 and 3 in direction X2) so as to force positioning-member connector 140 in direction X2. As positioning-member connector 140 is forced in direction X2, primary positioning member 132A and secondary positioning member 132B may simultaneously rotate about primary pivot 134A and secondary pivot 134B in rotational direction R3 and rotational direction R4, respectively. As shown in FIG. 5, rotational direction R3 may be opposite rotational direction R4. Positioning-member connector 140 may be connected to and/or integrally formed with end portions of extending surface 136A and extending surface 136B to facilitate rotation of primary positioning member 132A and secondary positioning member 132B. Additionally, spring 148 may move facial interface 110 in direction X2 by applying tension to facial interface 110 in direction X2 as a portion of spring 148 coupled to actuation member 142 and/or positioning-member connector 140 is stretched and tensioned in direction X2 by actuation member 142 and/or positioning-member connector 140.

In the contracted holding position illustrated in FIG. 5, contracting surface 138A and contracting surface 138B of primary positioning member 132A and secondary positioning member 132B, respectively, may face and abut positioning abutment surface 128 of facial interface 110 such that positioning abutment surface 128 is disposed at a contracted radial distance D2, which is less than extended radial distance D1 shown in FIG. 4, from primary pivot 134A and/or secondary pivot 134B. When facial-interface adjustment apparatus 130 is in the contracted holding position, facial interface 110 may be disposed at a contracted position relative to head-mounted-display housing 116 as illustrated, for example, in FIG. 3.

While facial-interface adjustment apparatus 130 is disposed in the contracted holding position, a force may be applied by the user's face to facial-abutment surface 124 of facial interface 110 in direction X2 while the user is wearing a head-mounted-display system (e.g., head-mounted-display system 100 shown in FIG. 1) that includes facial interface 110 and facial-interface adjustment apparatus 130. Facial-interface adjustment apparatus 130 may be prevented from moving from the contracted holding position shown in FIG. 5 to the extended holding position shown in FIG. 4 by the force applied by the user's face to facial interface 110 and/or by the force applied by tensioned spring 148 to facial interface 110 in direction X2. In some embodiments, actuation member 142 may be secured in a fixed position (e.g., by a holding feature in head-mounted-display housing 116 of head-mounted-display device 102) to prevent movement of actuation member 142 and thus maintain facial-interface adjustment apparatus 130 in the contracted holding position until the user manually moves actuation member 142 from the fixed position. Accordingly, the user may comfortably and securely mount the head-mounted-display system to their head when facial-interface adjustment apparatus 130 is in the contracted holding position.

Figure 6:
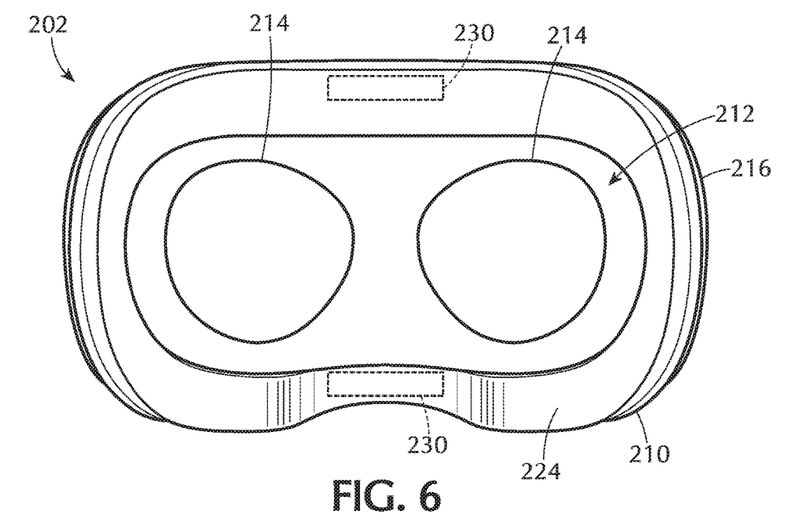
FIG. 6 is a front view of an exemplary head-mounted-display device in accordance with some embodiments.
Figure 7:
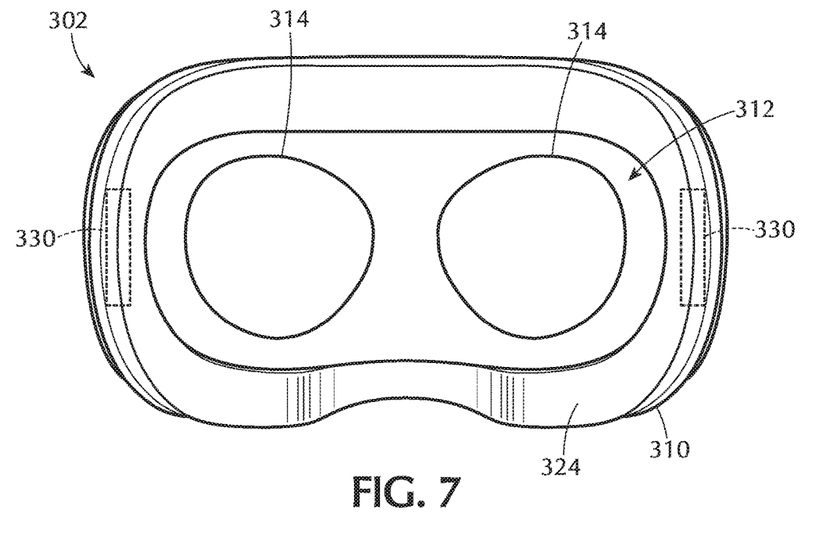
FIG. 7 is a front view of an exemplary head-mounted-display device in accordance with some embodiments.

FIGS. 6 and 7 show exemplary head-mounted displays having facial-interface adjustment apparatuses that are disposed in various configurations. Head-mounted displays may include facial-interface adjustment apparatuses that are disposed adjacent to portions of facial interfaces configured to abut various user facial regions, including nasal, cheek, temple, and/or forehead facial regions. Head-mounted displays, as disclosed herein, may include any suitable number of facial-interface adjustment apparatuses disposed at any suitable locations, without limitation. FIG. 6 shows a front view of a head-mounted-display device 202 having a facial interface 210 that surrounds a viewing region 212, which allows a user to view content displayed through lenses 214. Head-mounted-display device 202 may include a plurality of facial-interface adjustment apparatuses 230, with each facial-interface adjustment apparatus 230 including at least one positioning member (e.g., primary positioning member 132A and/or secondary positioning member 132B shown in FIGS. 2-5) disposed adjacent to facial interface 210. For example, as shown in FIG. 6, head-mounted-display device 202 may include at least two facial-interface adjustment apparatuses 220 disposed adjacent to portions of facial interface 210 that abut a nasal region and a forehead region of the user's face when the user wears head-mounted-display device 202.

FIG. 7 shows a front view of a head-mounted-display device 302 having a facial interface 310 that surrounds a viewing region 312, which allows a user to view content displayed through lenses 314. Head-mounted-display device 302 may include a plurality of facial-interface adjustment apparatuses 320, with each facial-interface adjustment apparatus 320 including at least one positioning member disposed adjacent to facial interface 310. For example, as shown in FIG. 7, head-mounted-display device 302 may include at least two facial-interface adjustment apparatuses 320 disposed adjacent to portions of facial interface 310 that abut left and right temple regions of the user's face when the user wears head-mounted-display device 302.

Figure 8:
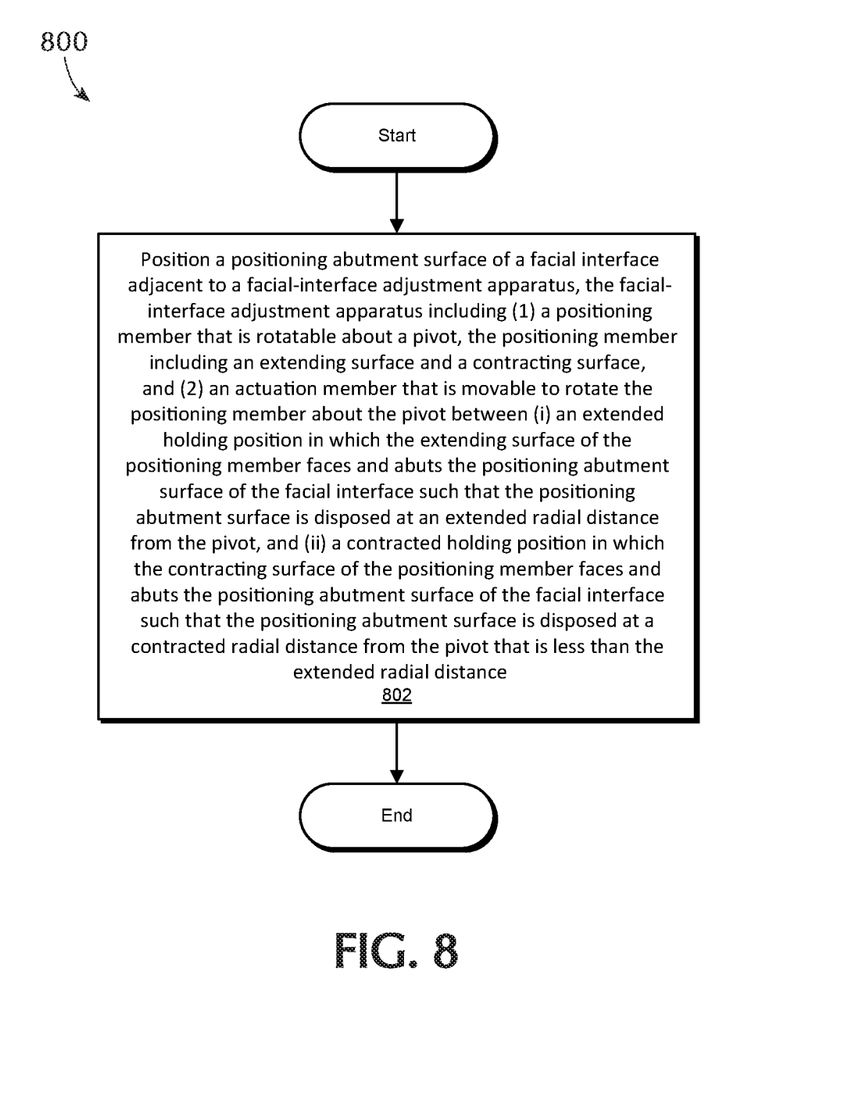
FIG. 8 is a block diagram of an exemplary method for assembling a facial-interface system for a head-mounted display in accordance with some embodiments.

FIG. 8 is a flow diagram of an exemplary method 800 for assembling a facial-interface system for a head-mounted display according to any of the embodiments disclosed herein. The steps shown in FIG. 8 may be performed by an individual and/or by any suitable manual and/or automated apparatus.

At step 802 in FIG. 8, a positioning abutment surface of a facial interface may be positioned adjacent to a facial-interface adjustment apparatus. The facial-interface adjustment apparatus may include (1) a positioning member that is rotatable about a pivot, the positioning member including an extending surface and a contracting surface and (2) an actuation member that is movable to rotate the positioning member about the pivot between (i) an extended holding position in which the extending surface of the positioning member faces and abuts the positioning abutment surface of the facial interface such that the positioning abutment surface is disposed at an extended radial distance from the pivot, and (ii) a contracted holding position in which the contracting surface of the positioning member faces and abuts the positioning abutment surface of the facial interface such that the positioning abutment surface is disposed at a contracted radial distance from the pivot that is less than the extended radial distance For example, positioning abutment surface 128 of facial interface 110 may be positioned adjacent to facial-interface adjustment apparatus 130, which includes primary positioning member 132A and secondary positioning member 132B that are respectively rotatable about primary pivot 134A and secondary pivot 134B (see, e.g., FIGS. 2-5). Primary positioning member 132A may include extending surface 136A and contracting surface 138A and secondary positioning member 132B may include extending surface 136B and contracting surface 138B (see, e.g., FIGS. 2-5). Facial-interface adjustment apparatus 130 may also include actuation member 142 that is movable to rotate primary positioning member 132A and secondary positioning member 132B respectively about primary pivot 134A and secondary pivot 134B between an extended holding position and a contracted holding position (see, e.g., FIGS. 2-5).

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

As discussed throughout the instant disclosure, the disclosed methods, systems, and devices may provide one or more advantages over traditional facial-interface systems. For example, the facial-interface systems described herein may include facial-interface adjustment apparatuses that enable users to quickly and easily adjust facial interfaces. The facial-interface adjustment apparatuses may each include one or more positioning members that are rotatable between an extended holding position that holds a facial interface at an extended position and a contracted holding position that holds a facial interface at a contracted position. The facial-interface systems may thus enable users to position the facial interfaces so as to comfortably fit head-mounted displays to various user face sizes and shapes. The facial-interface systems may also enable users to wear accessories, such as glasses, while wearing the head-mounted displays. Accordingly, the facial-interface systems may allow users to adjust and comfortably wear head-mounted displays without having to replace the facial interfaces and/or interface cushions.

The foregoing description, for purposes of explanation, has been described with reference to specific embodiments and has been provided to enable others skilled in the art to best utilize various aspects of the example embodiments disclosed herein. However, the illustrative discussions above are not intended to be exhaustive or to limit the scope of the claims to the precise forms disclosed. Many modifications and variations are possible in view of the above teachings without departing from the spirit and scope of the instant disclosure. The instant disclosure covers all modifications, equivalents, and alternatives falling within the scope of the appended claims. Features from any of the above-mentioned embodiments may be used in combination with one another in accordance with the general principles described herein. The embodiments were chosen to best explain the principles underlying the claims and their practical applications, to thereby enable others skilled in the art to best use the embodiments with various modifications as are suited to the particular uses contemplated. The embodiments disclosed herein should be considered in all respects illustrative and not restrictive. Reference should be made to the appended claims and their equivalents in determining the scope of the instant disclosure.

It will also be understood that, although the terms first, second, primary, secondary, etc. are, in some instances, used herein to describe various elements, these elements should not be limited by these terms. These terms are used only to distinguish one element from another. For example, a first segment could be termed a second segment, and, similarly, a second segment could be termed a first segment, without departing from the scope of the various described embodiments. The first segment and the second segment are both segments, but they are not the same segment.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "exemplary" is used herein in the sense of "serving as an example, instance, or illustration" and not in the sense of "representing the best of its kind." Unless otherwise noted, the terms "connected to," "coupled to," and "attached to" (and their derivatives), as used in the specification and claims, are to be construed as permitting both direct and indirect (i.e., via other elements or components) connection. Furthermore, two or more elements may be coupled together with an adhesive, a clasp, a latch, a hook, a link, a buckle, a bolt, a screw, a rivet, a snap, a catch, a lock, or any other type of fastening or connecting mechanism.

What is claimed is:

1. A facial-interface system for a head-mounted display comprising:
    a facial interface having a positioning abutment surface; and
    a facial-interface adjustment apparatus comprising:
        a positioning member that is rotatable about a pivot, the positioning member comprising an extending surface and a contracting surface; and
        an actuation member that that is movable to rotate the positioning member about the pivot between:
            an extended holding position in which the extending surface of the positioning member faces and abuts the positioning abutment surface of the facial interface such that the positioning abutment surface is disposed at an extended radial distance from the pivot; and
            a contracted holding position in which the contracting surface of the positioning member faces and abuts the positioning abutment surface of the facial interface such that the positioning abutment surface is disposed at a contracted radial distance from the pivot that is less than the extended radial distance.

2. The facial-interface system of claim 1, wherein the contracting surface extends from a region adjacent the extending surface to a portion of the positioning member adjacent the pivot.

3. The facial-interface system of claim 1, wherein the facial interface is movable between the extended holding position and the contracted holding position in a direction generally perpendicular to an axis of rotation of the positioning member about the pivot.

4. The facial-interface system of claim 1, wherein:
the positioning member comprises a wedge-shaped member tapering from the extending surface to a pivot region surrounding the pivot; and
the extending surface has a greater width than the pivot region.

5. The facial-interface system of claim 1, wherein the actuation member is movable in a direction generally perpendicular to an axis of rotation of the positioning member about the pivot.

6. The facial-interface system of claim 1, wherein the actuation member comprises a shaft portion that extends in a direction generally perpendicular to an axis of rotation of the positioning member about the pivot.

7. The facial-interface system of claim 1, wherein the facial-interface adjustment apparatus further comprises a spring that is coupled to the actuation member.

8. The facial-interface system of claim 7, wherein the spring is disposed between the actuation member and the facial interface.

9. The facial-interface system of claim 7, wherein:
the spring is relaxed when the positioning member is disposed in the extended holding position; and
the spring is tensioned when the positioning member is disposed in the contracted holding position.

10. The facial-interface system of claim 1, further comprising a restraining protrusion extending from the positioning abutment surface, wherein the contracting surface of the positioning member faces the restraining protrusion when the positioning member is disposed in the extended holding position.

11. The facial-interface system of claim 1, wherein:
the positioning member is a primary positioning member and the pivot is a primary pivot;
the facial-interface adjustment apparatus further comprises a secondary positioning member that is rotatable about a secondary pivot, the secondary positioning member comprising an extending surface and a contracting surface; and
the actuation member is movable to simultaneously rotate the secondary positioning member about the secondary pivot in conjunction with the rotation of the primary positioning member about the primary pivot such that the secondary positioning member rotates between:
an extended holding position in which the extending surface of the secondary positioning member faces and abuts the positioning abutment surface of the facial interface; and
a contracted holding position in which the contracting surface of the secondary positioning member faces and abuts the positioning abutment surface of the facial interface.

12. The facial-interface system of claim 11, further comprising a positioning-member connector that is connected to the primary positioning member and the secondary positioning member.

13. The facial-interface system of claim 12, wherein the positioning-member connector is connected to the extending surface of the primary positioning member and the extending surface of the secondary positioning member.

14. The facial-interface system of claim 12, wherein the positioning-member connector comprises a flexible material that folds as each of the primary positioning member and the secondary positioning member rotates from the extended holding position to the contracted holding position.

15. The facial-interface system of claim 12, wherein the actuation member is coupled to the positioning-member connector at a location between the primary positioning member and the secondary positioning member.

16. The facial-interface system of claim 11, wherein the actuation member simultaneously rotates the primary positioning member and the secondary positioning member in opposite rotational directions.

17. A head-mounted-display device comprising:
a head-mounted-display housing;
a facial interface having a positioning abutment surface; and
a facial-interface adjustment apparatus that is coupled to the head-mounted-display housing, the facial-interface adjustment apparatus comprising:
a positioning member that is rotatable about a pivot, the positioning member comprising an extending surface and a contracting surface; and
an actuation member that is movable to rotate the positioning member about the pivot between:
an extended holding position in which the extending surface of the positioning member faces and abuts the positioning abutment surface of the facial interface such that the positioning abutment surface is disposed at an extended radial distance from the pivot; and
a contracted holding position in which the contracting surface of the positioning member faces and abuts the positioning abutment surface of the facial interface such that the positioning abutment surface is disposed at a contracted radial distance from the pivot that is less than the extended radial distance.

18. The head-mounted-display device of claim 17, wherein the facial interface is disposed at a separate location relative to the head-mounted-display housing when the positioning member is disposed in each of the extended holding position and the contracted holding position.

19. The head-mounted-display device of claim 17, wherein the contracting surface extends from a region adjacent the extending surface to a portion of the positioning member adjacent the pivot.

20. A method comprising:
positioning a positioning abutment surface of a facial interface adjacent to a facial-interface adjustment apparatus, the facial-interface adjustment apparatus comprising:
a positioning member that is rotatable about a pivot, the positioning member comprising an extending surface and a contracting surface; and
an actuation member that is movable to rotate the positioning member about the pivot between:
an extended holding position in which the extending surface of the positioning member faces and abuts the positioning abutment surface of the facial interface such that the positioning abutment surface is disposed at an extended radial distance from the pivot; and
a contracted holding position in which the contracting surface of the positioning member faces and abuts the positioning abutment surface of the facial interface such that the positioning abutment surface is disposed at a contracted radial distance from the pivot that is less than the extended radial distance.

* * * * *